United States Patent [19]
Grompe

[11] Patent Number: 6,132,708
[45] Date of Patent: Oct. 17, 2000

[54] LIVER REGENERATION USING PANCREAS CELLS

[75] Inventor: Markus Grompe, Portland, Oreg.

[73] Assignee: Oregon Health Sciences University, Portland, Oreg.

[21] Appl. No.: 08/949,067

[22] Filed: Oct. 10, 1997

[51] Int. Cl.⁷ .............................. A01N 63/00; C12N 5/08
[52] U.S. Cl. ..................... 424/93.1; 435/325; 424/93.21; 424/93.7
[58] Field of Search ................................. 424/93.1, 43.2, 424/93.21, 93.7; 435/325

[56] References Cited

U.S. PATENT DOCUMENTS 5,770,417  6/1998  Vacanti et al. ........................... 435/180

FOREIGN PATENT DOCUMENTS

| WO 94/02601 | 2/1994 | WIPO . |
| WO 94/16059 | 7/1994 | WIPO . |
| WO 96/24669 | 8/1996 | WIPO . |
| WO 96/40872 | 12/1996 | WIPO . |

OTHER PUBLICATIONS

Aterman et al., "The stem cells of the liver—a selective review" *J. Cancer Res. Clin. Oncol.* (1992) 118:87–115.
Chen et al., "Hepatocytic differentiation of cultured rat pancreatic ductal epithelial cells after in vivo implantation" *Am. J. Pathol.* (1995) 147(3):707–717.
Dabeva et al., "Pancreatic epithelial progenitor cells differentiate into mature hepatocytes following transplantation into the rat liver" *J. Invest. Med.* (1996) 44(3):302A.
Dabeva et al., "Transcription factor and liver–specific mRNA expression in faculative epithelial progenitor cells of liver and pancreas" *Am. J. Pathol.* (1995) 147(6):1633–1648.
Grompe et al., "Loss of fumarylacetoacetate hydrolase is responsible for the neonatal hepatic dysfunction phenotype of lethal albino mice" *Genes & Dev.* (1993) 7:2298–2307.
Grompe et al., "Pharmacological correction of neonatal lethal hepatic dysfunction in a murine model of hereditary tyrosinaemia type I" *Nature Genet.* (1995) 10:453–460.
Heckel et al., "Neonatal bleeding in transgenic mice expressing urokinase–type plasminogen activator" *Cell* (1990) 62:447–456.
Jalan and Hayes, "Review article: quantitative tests of liver function" *Aliment. Pharmacol. Ther.* (1995) 9:263–270.
Lalwani et al., "Development of hepatocellular carcinomas and increased peroxisomal fatty acid β–oxidation in rats fed [4–chloro–6–(2,3–xylidino)–2–pyrimidinylthio] acetic acid (Wy–14,643) in the semipurified diet" *Carcinogenesis* (1981) 2(7):645–650.
Michaelopolous and DeFrances, "Liver regeneration" *Science* (1997) 276:60–65.
Mullen et al., "Transfer of the bacterial gene for cytosine deaminase to mammalian cells confers lethal sensitivity to 5–fluorocytosine: A negative selection system" *Proc. Natl. Acad. Sci. USA* (1992) 89:33–37.
Overturf et al., "Adenovirus–mediated gene therapy in a mouse model of hereditary tyrosinemia type I" *Human Gene Ther.* (1997) 8:513–521.
Overturf et al., "Hepatocytes corrected by gene therapy are selected in vivo in a murine model of hereditary tyrosinaemia type I" *Nature Genet.* (1996) 12:266–273.
Potten and Loeffler, "Stem cells: attributes, cycles, spirals, pirfalls and uncertainties. Lessons for and from the crypt" *Development* (1990) 110:1001–1020.
Rao et al., "Role of periductal and ductular epithelial cells of the adult rat pancreas in pancreatic hepatocyte lineage" *Am. J. Pathol.* (1989) 134(5):1069–1086.
Reddy et al., "Pancreatic hepatocytes. An in vivo model for cell lineage in pancreas of adult rat" *Digestive Dis. Sci.* (1991) 36(4):502–509.
Rhim et al., "Replacement of diseased mouse liver by hepatic cell transplantation" *Science* (1994) 263:1149–1152.
Sandgren et al., "Complete hepatic regeneration after somatic deletion of an albumin–plasminogen activator transgene" *Cell* (1991) 66:245–256.
Scarpelli et al., "Differentiation of regenerating pancreatic cells into hepatocyte–like cells" *Proc. Natl. Acad. Sci. USA* (1981) 78(4):2577–2581.
Sigal et al., "Demonstration of differentiation in hepatocyte progenitor cells using dipeptidyl peptidase IV deficient mutant rats" *Cell. Mol. Biol. Res.* (1995) 41(1):39–47.
Mirčetić, R.N. et al., "Glycolysis and Gluconeogenesis in Experimental Diabetes" *Diabetologia Croatica* 21(1/2):19–23 (1992).
Orkin et al. Report and Recommendations of the Panel to Assess the NIH Investment in Research on Gene Therapy. Distributed by the National Institutes of Health, Bethesda, MD or www.nih.gov., Dec. 7, 1995.
Verma et al. Gene Therapy Promises, Problems, and Prospects. Nature, vol. 389, pp. 239–242, Sep. 18, 1997.
Crystal, R. G. Transfer of Genes to Humans: Early Lessons and Obstacles to Success. Science, vol. 270, pp. 404–410, Oct. 20, 1995.
Stedman's Medical Dictionary, 26th Edition, Williams & Wilkins. pp. 50 and 1966, 1995.
Hadji–Georgopoulos et al. Endocrine and Exocrine Function of Intrasplenic Pancreatic Autografts. Surgery, vol. 91, No. 2, pp. 210–216, 1982.

*Primary Examiner*—Deborah J. Clark
*Attorney, Agent, or Firm*—Morrison & Foerster, LLP

[57] ABSTRACT

This invention provides a method of regenerating a functional liver by transplantation of pancreas cells. Also provided are pancreas cell capable of regenerating functional liver tissue.

16 Claims, 3 Drawing Sheets

LIVER REGENERATION USING PANCREAS CELLS

STATEMENT OF RIGHTS TO INVENTIONS MADE UNDER FEDERALLY SPONSORED RESEARCH

This invention was made in part during work supported by a grant from the National Institutes of Health DK48252. The government has certain rights in this invention.

TECHNICAL FIELD

This invention is in the field of liver regeneration. In particular, the present invention provides methods of regenerating liver function using pancreas cells.

BACKGROUND

The search for effective treatments for liver disease remains a challenging medical issue. There are many causes of liver failure including anatomical defects leading to progressive liver disease, drug induced liver injury, metabolic liver disease, hepatic neoplasms, vascular injury affecting the liver and viral hepatitis. Known hepatitis vaccines are not always available and hepatitis C, for instance, kills an estimated 8,000–10,000 people in the United States per year. Without effective intervention that number is predicted to triple in the next 10–20 years. National Institutes of Health, Consensus Development Statement, "Management Of Hepatitis C" Mar. 24–26, 1997.

Although the liver has tremendous capacity to regenerate itself, liver damage can inhibit or abolish this regenerative capacity. There is currently no machine which is able to replace liver function. Currently, the only effective treatment for liver failure is to perform a liver transplant.

In 1994, only 10% (approximately 3,652 people) of those awaiting donor livers received a transplant. (United Network for Organ Sharing, UNOS). In addition, there are many complications associated with liver transplants. Even after matching donor and recipient, rejection of the graft organ often occurs. Immunosuppressants given to reduce the chance of graft rejection cause their own set of problems. Graft versus Host Disease (GVHD), a harmful immune system effect where lymphocytes within tissue that was grafted from a different individual attacks the tissue in its new location can also occur.

Due to the severe shortage of donor livers and complications of associated with transplants, an alternative to human liver transplantation would save many patients from suffering and premature death associated with acute liver failure. Health expenditures would also be reduced, as liver transplants are currently performed at an average cost of approximately $150,000 per transplant. PROGRESS (1997), American Liver Foundation. An alternative to liver transplantation that avoids host immune rejection would therefore be particularly useful.

A great deal of attention has been focused on the possibility of treating liver failure with regenerative hepatocytes. Grompe et al. (1997), *Amer. J. Pathol.*, in press, have shown that a single mouse hepatocyte can expand through at least 69 cell divisions, generating $7 \times 10^{20}$ cells. Since an average mouse liver contains approximately $3 \times 10^7$ hepatocytes, one hepatocyte has the capacity to generate a number of cells equivalent to $10^{13}$ mouse livers. However, relative to other regenerative tissues, liver regeneration is a complex response involving proliferation of all the existing mature cells of the liver, rather than on a small group of progenitor cells. Michaelopolous et al. (1997) *Science* 276:60–65. Liver stem cells have not been identified microscopically and it is postulated that they may not exist due to the long life span of hepatocytes as well as differentiated hepatocytes' ability to regenerate in response to liver cell loss. Aterman et al. (1992) *J. Cancer Res. Clin. Oncol.* 118:87–115; Potten et al. (1990) *Development* 110:1001–1020.

In order to test liver regenerative capability, several animal models have been generated. A transgenic mouse bearing the urokinase-type plasminogen activator (uPA) coding sequence fused to the albumin (Alb) enhancer/promoter causes neonatal hemorrhaging in mice hepatocytes. Heckel et al. (1990) *Cell* 62:447–456. While this mouse model has been used in the study of the regenerative potential of transplanted hepatocytes (Sandgren et al. (1991) *Cell* 66:245–256; Rhim et al. (1994) *Science* 263:1149–1152; WO 94/02601), there are disadvantages in using this mouse to show that transplanted cells can restore liver function. In particular, the toxic uPA transgene is deactivated by DNA rearrangement in isolated hepatocytes which in turn leads to repopulation of the entire liver by cells that do not express uPA. As a result of this loss of the transgene, only one half of the transgenic mice die at birth, while the other half survives and expresses normal plasma uPA concentrations within 2 months of birth. Sandgren et al. (1991), supra.

A mouse model of a human liver disease has recently been developed by the present inventor which is useful for examining the restoration of liver function. Hereditary Tyrosinemia type I (HT1) is a metabolic disease caused by a lack of the enzyme fumarylacetate hydrolase (FAH) and is characterized by severe liver dysfunction in childhood, renal tubular damage, and hepatocellular cancer. The development of the FAH-mutant mouse model (Grompe et al. (1993) *Genes & Dev.* 7:2298–2307) is especially useful because therapy for HT is usually human liver transplantation. Treatment with the drug NTBC (2-(2-nitro-4-triflouro-methylbenzoyl)-1,3-cyclohexedione) prevents the neonatal lethality and liver dysfunction in the transgenic mouse. When NTBC is withdrawn, the FAH-mutant mice develop a liver dysfunction with a similar phenotype to humans suffering from HT. Grompe et al. (1995) *Nature Genet.* 10:453–460.

The FAH deficient mouse model has several advantages over the urokinase model described above. First, the viability of the urokinase transgenics is low and surgical procedures are difficult because of the systemic bleeding induced by this secreted protein. In contrast, NTBC treated FAH mutant mice are healthy and viable. Second, there is a high rate of spontaneous reversion (loss of the transgene) in the urokinase transgenics, so that the liver of these animals will have self-corrected by the time the animals are 1 month old. (Rhim et al. (1994) *Science* 263:1149–1152; Sandgren et al. (1991) *Cell 66:245–256*). For this reason, transplantation of wild-type cells into urokinase mice must take place very early in life, usually at less than 15 days in order for selection to take place. This makes surgical manipulations such as intraportal injections difficult. In contrast, FAH deficient animals can be kept on NTBC as long as desired and then transplanted as adults. The mutation in the FAH mice (FAH$\Delta^{exon5}$) does not spontaneously revert. Accurate quantification of nodules is also a problem in the urokinase transgenic model because the spontaneous reversions make it difficult to distinguish nodules arising from transplanted cells from nodules arising from reversion.

A third advantage of the FAH system is that the selective pressure in FAH mutant mice can be turned off or on using either NTBC or homogentisic acid. This permits flexibility in the selection process, an important consideration for successful xenograft experiments. If, for example, the transplanted cells take time to repopulate, a low level or intermittent NTBC treatment will allow the recipient animals to survive while selection is occurring. Fourth, the selection in FAH deficiency is a positive selection for an added gene. FAH deficient cells can be transduced and marked with an FAH expressing construct, such as retroviruses. The ability to tag cells is invaluable in lineage experiments. In contrast, selection in the urokinase system is a negative selection for the loss or absence of the transgene and selection for retroviral marking is impossible.

A further advantage of the FAH mouse model is that HTI, with its high α-fetoprotein level and continuous liver regeneration, represents exactly the kind of pathological condition in which one would expect facultative liver cells to be activated. The autocrine and paracrine growth environment in these livers is likely to the meet the requirements for expansion and growth of progenitor cells, including from xenogenic sources.

Using the FAH-mutant model, researchers have shown that wild-type hepatocytes have a selective advantage over FAH deficient cells and can repopulate the liver when mice are removed from NTBC. Overturf et al. (1996) *Nature Genet*. 12:266–273 This model has also been used to show that hepatocytes can be corrected by gene therapy with a recombinant adenovirus expressing FAH. Overturf et al. (1997) *Human Gene Ther*. 8:513–521. In addition, Overturf et al. (1996), *Nature Genet*. 12:266 report that as few as 1000 hepatocytes can restore liver structure and function in a mouse liver. More than 90% of the resulting hepatocytes were found to be FAH positive.

However, the applicability of these hepatocyte studies is limited as most patients with liver failure do not have enough unaffected hepatocytes to regenerate a healthy, functioning liver. As described above, transplantation of heterologous liver cells involves significant risk associated with the host's immune rejection of the transplanted cells. Therefore, it would be useful to have an autologous source of unaffected cells capable of repopulating the liver.

Scarpelli et al. (1981) *PNAS* 78:2577 describe how acinar pancreas cells treated with the carcinogen N-nitroso-bis(2-oxopropyl)amine (BOP) appear similar to hepatocytes. Similarly, Lalwani et al. (1981) *Carcinogenesis* 2:645 describe how hepatocyte-like cells can be induced in the pancreas of rats by feeding the animals a diet containing (4-chloro-6-(2,3-xylidino)-2pyrimidinylthio) acetic acid, a peroxisome proliferator. Reddy et al. (1991) *Digestive Dis. Sci*. 36(4):502 describe methods of inducing hepatocyte-like cells in rat pancreas by maintaining the rats on a copper-deficient diet containing the copper chelator, triethylenetetramine tetrahydrochloride (trien). Under these conditions, the pancreatic acinar cells are depleted and hepatocyte-like cells appear. Rao et al. (1989) *Am. J. Pathol*. 134(5):1069–1086 report that after 8 weeks on the copper-deficient diet 60% of the volume of the pancreas was occupied by hepatocyte-like cells. These studies do not report on the function of either the pancreas or the liver.

Dabeva et al. (1995) *Am J. Pathol*. 147:1633–1648 describe how pancreatic epithelial cells transplanted into the livers of rats proliferate and express liver specific genes. Chen et al. (1995) *Am J. Pathol*. 147(3):707–717 describe how rat pancreatic epithelial cells genetically labeled with β-galactosidase resemble hepatocytes 4 to 8 weeks after transplantation into rat livers. Pancreatic epithelial progenitor cells, identified by their expression of dipeptidyl peptidase IV (DPPIV), were transplanted into the livers of DPPIV-mutant rats and found by histochemical analysis to show characteristics of mature hepatocytes and physical continuity with endogenous hepatocytes within the liver plates. Sigal et al. (1995) *Cell. Mol. Biol. Res*. 41(1):39–47; Dabeva et al. (1996) *J. Invest. Med*. 44(3):206A.

WO 96/40872 describes methods for isolation and in vitro expansion of pancreatic progenitor cells isolated from the bile duct. In this system, the pancreas cell population is contacted with a proliferative agent such as a growth factor that specifically stimulates growth of certain distinct groups of pancreatic progenitor cells. Progenitor cells within the culture are identified by changes in cell proliferation and morphology. The pancreatic progenitors are then isolated from other pancreatic cells using techniques based on specific cellular markers. Progenitor cells which differentiate into pancreatic islet cells or hepatocytes and are identified by the expression of various specific cellular markers can be further cultured under conditions allowing differentiation into various cell lineages such as hepatic and pancreatic. This method does not assay the ability of cells to regenerate a functioning liver because the pancreatic progenitor cells and hepatocytes are characterized only by their physical appearance and cellular markers. Thus, these studies do not provide evidence that transplanted cells have the ability to restore liver function.

SUMMARY OF THE INVENTION

The present inventor is the first to describe and demonstrate that pancreas cells can be used to regenerate liver tissue and that these pancreas cells are capable of restoring liver function.

In one aspect the present invention includes a method of regenerating liver function in an individual, the method comprising (a) introducing an effective amount of pancreas cells into the individual; and (b) allowing the pancreas cells to regenerate at least one liver function. In one embodiment, the individual is a mammal, preferably a human.

In another preferred embodiment, the pancreas cells are introduced into the spleen of the individual. In another aspect, the pancreas cells are an autograft (i.e. from the same individual). Alternatively, the pancreas cells are an allograft (i.e. from a different individual). In yet another preferred embodiment, the pancreas cells are modified by gene transfer. The pancreas cells can also be cultured in vitro to form stable cell lines which are then introduced into the individual to regenerate liver function.

In another aspect, the invention includes a method of treating liver disease in an individual, the method comprising introducing pancreas cells into the individual, wherein the pancreas cells are capable of regenerating liver function. In a preferred embodiment, the individual is a human. In another preferred embodiment, the pancreas cells are introduced into the spleen of the individual. In one aspect, the pancreas cells are an allograft. Alternatively, the pancreas cells are autograft. In other embodiments, the pancreas cells are modified by gene transfer or are obtained from in vitro cultures. In another preferred embodiment, the liver disease to be treated is selected from the group consisting of hereditary tyrosinaemia type 1 (HT1), cirhhosis, liver cancer and hepatitis.

In another aspect, the invention includes pancreas cells capable of regenerating liver function, the pancreas cells prepared by (a) isolating pancreas tissue from an individual; and (b) preparing cell suspensions of the cells. In other embodiments, the pancreas cells are further modified by gene transfer or are cultured in vitro. Compositions comprising the cells prepared according to the invention are also provided.

As will become apparent, preferred features and characteristics of one aspect of the invention are applicable to any other aspect of the invention.

MODES FOR CARRYING OUT THE INVENTION

Figure 1:
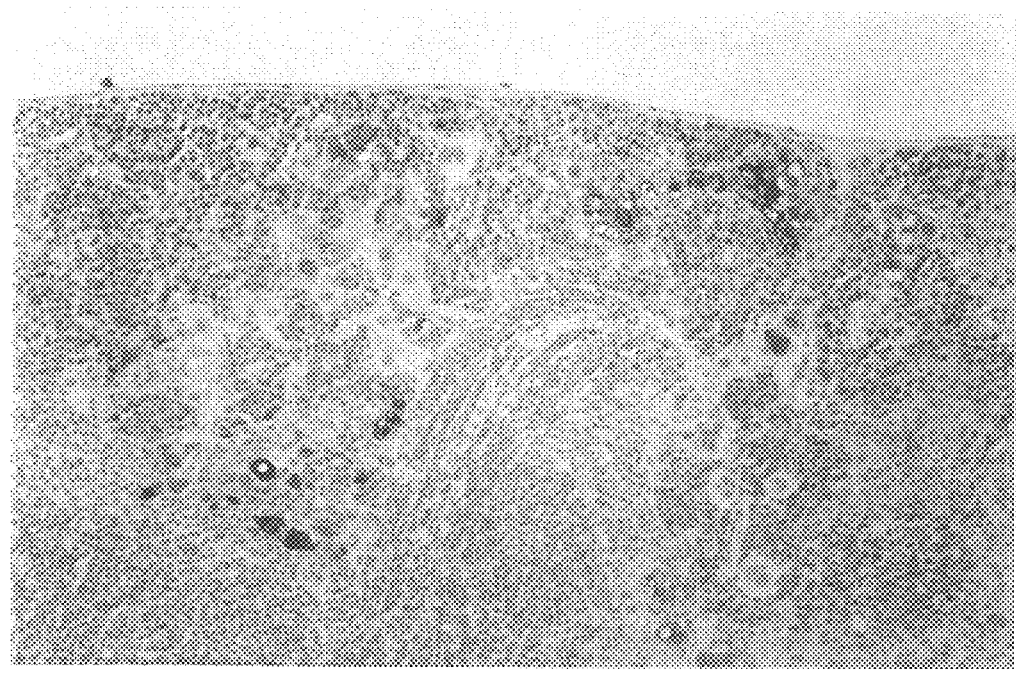
FIG. 1 is a half-tone reproduction depicting immunohistochemical staining for fumarylacetoacetate hydrolase (FAH) of spleen tissue from an FAH mutant mouse into which wild-type pancreas cell have been introduced. FAH-positive cells are present.

Throughout this application, various publications, patents, and published patent applications are referred to by an identifying citation. The disclosure of the publications, patents, and published patent specifications referenced in this application are hereby incorporated by reference into the present disclosure to more fully describe the state of the art to which this invention pertains.

As used herein, certain terms will have specific meanings.

As used herein, the term "regeneration" refers to the growth or proliferation of new tissue. In the present invention, regeneration refers to the growth and development of functional liver tissue. In most instances, the regenerated liver tissue will also have the cytological and histological characteristics of normal liver tissue. For example, the pancreas cells introduced in to the individual and allowed to generate functional liver tissue are expected to express FAH and H & E along with other markers indicative of liver function. In addition, these cells are also expected to perform one or more functions of the liver as measured by tests known in the art.

The phrase "liver function" refers to one or more of the many physiological functions performed by the liver. The liver is a large gland found in all vertebrates that performs over 100 specific functions, including but not limited to, control of carbohydrate metabolism (e.g., blood sugar levels, endocrine regulation, enzyme systems and negative feedback mechanisms); interconversion of metabolites (e.g., ketone bodies, sterols and steroids and amino acids); blood protein manufacture (the liver is the sole source of fibrinogen, serum albumin and cholinesterase); erythropoietic function; detoxification; bile formation and vitamin storage.

In vertebrates, all adult livers have essentially the same structure. In humans, the organ has a large right lobe and a smaller left lobe. The liver weighs about 3 pounds and is situated in the upper right side of the abdomen, mostly under the ribs. Arterial blood is supplied through the hepatic artery. Hepatic architecture is characterized by a continuous convoluted wall of functional parenchymal cells. A homogenous network of blood vessels and biliary tracts runs through the parenchymal cells, forming a maze of corridors known as the labyrinthus hepatus. The methods of the present invention are also capable of regenerating liver architecture and structure.

The cells making up the liver include hepatocytes (the main functional cells of the liver); Kupffer cells (macrophages); biliary epithelial cells (which form the lining of the biliary ducts); fenestrated endothelial cells (cells having large cytoplasmic gaps that allow maximal contact between circulating blood and hepatocytes); and cells of Ito (stellate cells that store vitamin A, synthesize connective tissue proteins and secrete several growth factors).

Liver function can be measured by a variety of quantitative and qualitative tests. Conventionally, the degree of liver impairment is assessed using tests which evaluate structure (e.g., biopsy), cellular permeability (e.g., transaminases) and synthetic ability (e.g, albumin, bilirubin and prothrombin time). Jalan and Hayes (1995) *Aliment. Pharmacol. Ther.* 9:263–270. Measurements of enzyme activity are static tests and, when used alone, may not reflect the functional capacity of the liver. However, a combination of various markers for liver injury may provide a more accurate picture of liver function, especially if serial determinations are conducted. The six most commonly used tests for liver clearance capability are: indocyanine green (ICG), galactose elimination capacity (GEC), mono-ethyl-glycine-xylidide (MEG-X), antipryine clearance, aminopyrine breath test (ABT) and caffeine clearance. (See, Jalan and Hayes, supra). For assessment of graft function following transplantation, low ICG clearance and low MEG-X formation may be predictive of a poor outcome.

As used herein, the phrase "liver disease" or "liver failure" refers to a wide variety of conditions which affect function of the liver. For example, in both Type A (infectious hepatitis) and Type B viral hepatitis (serum hepatitis), the lobular architecture of the liver may be distorted by an infiltration of inflammatory mononuclear cells. Drainage of bile through the ducts is impaired, resulting in accumulation of bile. Another group of chronic liver disease, referred to as cirrhosis, are characterized by wide-spread fibrosis of the liver and nodular regeneration of hepatic parenchymal cells. Primary liver cancer in the United States is generally associated with cirrhosis. Many liver tumors are metastatic from another primary site, particularly the lung and pancreas from which the liver received venous drainage. Other non-limiting examples of liver disease include Reye's syndrome in young children, Wilson's disease, hemochromatosis, alpha-1-antitrypsin deficiency and various parasitic infections. Liver disorders can also be genetic, for example hereditary tyrosinemia type I (HT-1).

As used herein, the term "introducing" means providing or administering to an individual. In the present invention, pancreas cells capable of regenerating functional liver cells are introduced into an individual. Methods of introducing cells into individuals are well known to those of skill in the art and include, but are not limited to, injection, intravenous or parenteral administration. Single, multiple, continuous or intermittent administration can be effected. Preferably, the pancreas cells are deposited in the spleen of the individual. The "spleen" is large lymphoid organ involved in hematopoiesis, particularly the production of lymphocytes. The spleen is also is involved in the destruction of erythrocytes as well as extrahepatic synthesis of bilirubin.

The term "pancreas" refers to a large, elongated yellowish gland found in vertebrates. The pancreas has both endocrine and exocrine functions, producing the hormones insulin and glucagon and, in addition, secreting digestive enzymes. The term "pancreas cells" or "pancreatic cells" refers to cells obtained from the pancreas.

An "effective amount" is an amount sufficient to effect beneficial or desired clinical results. An effective amount can be administered in one or more applications, although it is preferable that one administration will suffice. For purposes of this invention, an effective amount of pancreatic cells is an amount that is sufficient to produce hepatocytes which are able to restore one or more of the functions of the liver. It is contemplated that a restoration can occur quickly by the introduction of relatively large numbers of pancreas cells, for example greater than $10^9$ cells. In addition, it is also contemplated that when fewer pancreatic cells are introduced, function will be restored when the pancreas cell or cells are allowed to proliferate in vivo. Thus, an "effective amount" of pancreatic cells can be obtained by allowing as few as one pancreas cell sufficient time to regenerate all or part of a liver. The present inventor has shown in the mouse model that $10^3$ cells can regenerate an entire liver of $3 \times 10^7$ cells, or approximately 1.0 grams of tissue. Human livers weigh approximately 1.5 kilograms, therefore one administration of approximately $10^8$ cells is expected to regenerate an entire human liver. Preferably, an effective amount administered to the individual is greater than about $10^3$ pancreas cells, preferably between about $10^3$ and about $10^{12}$ pancreas cells and even more preferably, between about $10^6$ and about $10^9$ pancreas cells. In terms of treatment, an "effective amount" of pancreatic cells is the amount which is able to ameliorate, palliate, stabilize, reverse, slow or delay the progression of liver disease.

The term "treating" or "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

The term "individual" is a vertebrate, preferably a mammal, more preferably a human. Mammals include, but are not limited to, humans, rodents, farm animals, sport animals and pets.

The terms "autograft" refers to removal of part of an organism and its replacement in the body of the same individual. Thus, an autograft is the introduction of autologous organs, tissue or cells in one individual. The present invention includes, therefore, methods in which a portion of an individual's pancreas is removed and then these pancreatic cells are introduced back into the same individual to form functioning liver cells.

As used herein, the term "allograft" refers to the removal of part of one individual and its replacement in the body of a different individual. Allografts are also known as xenografts, heterografts or heterologous grafts. Allografts can be obtained from a variety of sources including conventional organ donation. Alternatively, since the pancreas can regenerate, living donors can provide a source of appropriate pancreas cells when only a small portion of the pancreas is removed.

As used herein, the term "gene therapy" or "gene transfer" is defined as the insertion of genes into cells for the purpose of medicinal therapy. There are many applications of gene therapy, particularly via stem cell genetic insertion, and thus are well known and have been extensively reviewed.

As used herein, the term "in vitro culture" refers to the survival of cells outside the body. Preferably, the cultures of the present invention are "long-term" cultures in that they proliferate stably in vitro for extended periods of time. Methods of maintaining long-term and stable in vitro cultures of various cells have been extensively reviewed and are well known to those in the art.

Isolation of Pancreas Cells

The present invention involves the use of pancreas cells to regenerate functional liver tissue. The pancreas cells used in the methods of the present invention may be obtained from a heterologous donor, for example, an organ donor or a living donor. Alternatively, an autograft can be performed by removing a portion of an individual's pancreas and introducing the pancreas cells capable of regenerating liver function into the same individual. For autografts, at least about 5% of the donor individual's pancreas is removed. For allografts, at least about 5%, preferably greater than 30%, more preferably greater than 50% and even more preferably greater than 80% of the pancreas is removed.

Suitable techniques for isolating pancreas tissue from a donor individual are known in the art. For example, extraction of pancreas cells through a biopsy needle or surgical removal of a portion or all of the pancreas tissue can be utilized.

Pancreatic tissue can be used in the methods of the present invention without further treatment or modification. Modifications are described below. For both modified and unmodified cells, it is preferred that single cell suspensions are obtained from the tissue. Cell suspensions can be obtained by methods known in the art, for example, by centrifugation and enzyme treatment. Pancreas tissue or cell suspensions can also be frozen and thawed before use. Preferably, the cells are used fresh after isolation and processing.

Alternatively, the pancreas cells of the present invention can be cultured long-term in vitro to produce stable lines of liver-regenerating cells. These stable populations of cells are capable of surviving and proliferating in vitro (i.e. these cells will be "stem" cells). Methods of culturing various types of stem cells are known in the art. For example, WO 94/16059 describes long-term culture (greater than 7 months) of neuronal cells. Long-term culture of other types of stem cells are also described in the art and can be applicable to the cells of the present invention.

Modification of Pancreas Cells

Before introduction into an individual, the isolated pancreas cells of the present invention can be further modified, for example, using particular cell culturing conditions or by genetic engineering techniques.

The isolated cells can be cultured in vitro prior to introduction into the individual. Suitable culture media are well known to those of skill in the art and may include growth factors or other compounds which enhance survival, proliferation or selectively promote the growth of certain cells such as the hepatocyte forming cells.

Genetic engineering techniques can be used to introduce genes to be expressed. The invention also encompasses treatment of diseases or amelioration of symptoms associated with disease, amenable to gene transfer into pancreas cell populations obtained by the methods disclosed herein.

For a number of diseases, the introduction of a normal copy or functional homolog of the defective gene and the production of even small amounts of the missing gene product would have a beneficial effect. At the same time, overexpression of the gene product would not be expected to have deleterious effects. Strategies to treat various forms of cancer also include gene therapy. The retroviral vector can carry a gene that encodes, for example, a toxin or an apoptosis inducer effective to specifically kill the cancerous cells. Specific killing of tumor cells can also be accomplished by introducing a suicide gene to cancerous hematopoietic cells under conditions that only the tumor cells express the suicide gene. The suicide gene product confers lethal sensitivity to the cells by converting a normally nontoxic drug to a toxic derivative. For example, the enzyme cytosine deaminase converts the nontoxic substance 5'-fluorocytosine to a toxic derivative, 5-fluorouracil (Mullen et al.(1992) *PNAS USA* 89:33–37).

Diseases related to the lack of a particular secreted product including, but not limited to, hormones, enzymes, interferons, growth factors, or the like can also be treated with genetically modified pancreas cells. By employing an appropriate regulatory initiation region, inducible production of the deficient protein can be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic or viral diseases.

The therapeutic gene is transduced into the cell by any number of methods, e.g., using naked polynucleotides (e.g., by electroporation) or using delivery systems such as adenoviral vectors, adeno-associated viral vectors, retroviral and liposomes. Adenoviral, vaccinia, canarypox viral, cationic liposomes and plasmids are useful to achieve transient expression. Overturf et al. (1997) *Human Gene Therapy*, 8:513–521 have recently demonstrated that FAH-expressing adenovirus can be used to successfully in mice to treat hereditary tyrosinemia type I (HT1). Preferably, retroviral vectors such as, Moloney Murine Leukemia Virus (MoMLV), Myeloproliferative Sarcoma Virus (MPSV), Murine Embryonic Stem Cell Virus (MESV) and adenovirus, are useful to achieve stable and sustained expression of the transferred gene or gene product. Direct physical methods also are available. These methods include the use of the "gene gun" or calcium phosphate transfection method.

As noted above, any method of gene transfer is encompassed by this invention. As used herein, "viral delivery system" is defined as a recombinantly produced virus (or viral particle) that comprises a polynucleotide to be delivered into a host cell, either in vivo, ex vivo or in vitro. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Therapeutic genes that encode dominant inhibitory oligonucleotides and peptides as well as genes that encode regulatory proteins and oligonucleotides also are encompassed by this invention. Generally, gene therapy will involve the transfer of a single therapeutic gene although more than one gene may be necessary for the treatment of particular diseases. In one embodiment, the therapeutic gene is a normal, i.e. wild-type, copy of the defective gene or a functional homolog. In a separate embodiment, the therapeutic gene is a dominant inhibiting mutant of the wild-type. More than one gene can be administered per vector or alternatively, more than one gene can be delivered using several compatible vectors. Depending on the genetic defect, the therapeutic gene can include the regulatory and untranslated sequences. The therapeutic gene suitable for use in treatment will vary with the disease.

Nucleotide sequences for the therapeutic gene will generally be known in the art or can be obtained from various sequence databases such as GenBank. The therapeutic gene itself will generally be available or can be isolated and cloned using the polymerase chain reaction PCR (Perkin-Elmer) and other standard recombinant techniques. The skilled artisan will readily recognize that any therapeutic gene can be excised as a compatible restriction fragment and placed in a vector in such a manner as to allow proper expression of the therapeutic gene.

A marker gene can be included in the vector for the purpose of monitoring successful transduction and for selection of cells into which the DNA has been integrated, as against cells which have not integrated the DNA construct. Various marker genes include, but are not limited to, antibiotic resistance markers, such as resistance to G418 or hygromycin. Less conveniently, negative selection may be used, including, but not limited to, where the marker is the HSV-tk gene, which will make the cells sensitive to agents such as acyclovir and gancyclovir.

When gene transfer is performed ex vivo, pancreas cells are harvested and prepared as described above. The cell population is then infected with the retroviral or other vectors carrying a suitable therapeutic gene.

Introduction of Pancreas Cells

The pancreas cells of the present invention may be introduced into a recipient individual using any method known in the art. Preferably, cell suspensions of from about $10^6$ to about $10^9$ cells are prepared and injected into the individual. The cells can be introduced into any of several different sites, including but not limited to the abdominal cavity, the kidney, the liver, the celiac artery, the portal vein or the spleen. Cells can be introduced by a variety of administration routes, including intravenously, intramuscularly or subcutaneously. Preferably, the cells are injected into the spleen, directly into the liver or into the portal vein.

The methods of the present invention involve either allograft or autografts of pancreas cells. Each type of graft has its advantages. In particular, autografts (where pancreas cells from the same individual are used to regenerate liver function) avoid immunological reactions. Graft versus host reactions occur when the donor and recipient are different individuals, and the donor's immune system mounts a response against the graft. Tissue typing and major histocompatibility (MHC) matching reduces the severity and incidence of graft versus host. Nonetheless, autologous introduction of pancreas cells will be especially useful in cases where the individual's liver is diseased, but their pancreas remains normal. In such cases, a small amount of autologous pancreas tissue will regenerate a functional liver.

Allografts are useful in cases where both the pancreas is not available, for instance if both the liver and the pancreas of the individual are diseased. Various MHC matched pancreas cells can be maintained in vitro or isolated from donors and tissue typing performed to match the donor with the recipient. Immunosuppressive drugs, such as cyclosporin, can also be administered to reduce the graft versus host reaction.

Allografts using the cells obtained by the methods of the present invention are also useful because a single healthy donor could supply enough cells to regenerate at least partial liver function in multiple recipients. Because the pancreas cells of the present invention are able to proliferate and differentiate so effectively, only a small number is required to repopulate a liver. Accordingly, one pancreas could be divided and used for multiple allografts. Similarly, a small number of cells from one pancreas could be culture in vitro and then used for multiple grafts.

Preferably, a sufficient number of pancreatic cells are used so that the recipient can be taken off drug or other therapies. However, if the number of transplanted cells is small, the recipient can be maintained on low or intermittent drug levels until the cells have produced sufficient progeny to generate a functional liver.

Regeneration of Liver Function

The pancreas cells used in the present invention are capable of regenerating liver function. It is the novel finding of the present inventor that pancreas cells are capable of rescuing individuals having non-functional livers. Although previous studies have shown that pancreas cells are capable of taking on the appearance of hepatocytes, none have shown that these cells can restore the complex function and structure of the liver. The present invention, therefore, provides the first evidence that adult pancreas cells can regenerate functioning liver tissue after implantation.

Figure 2:
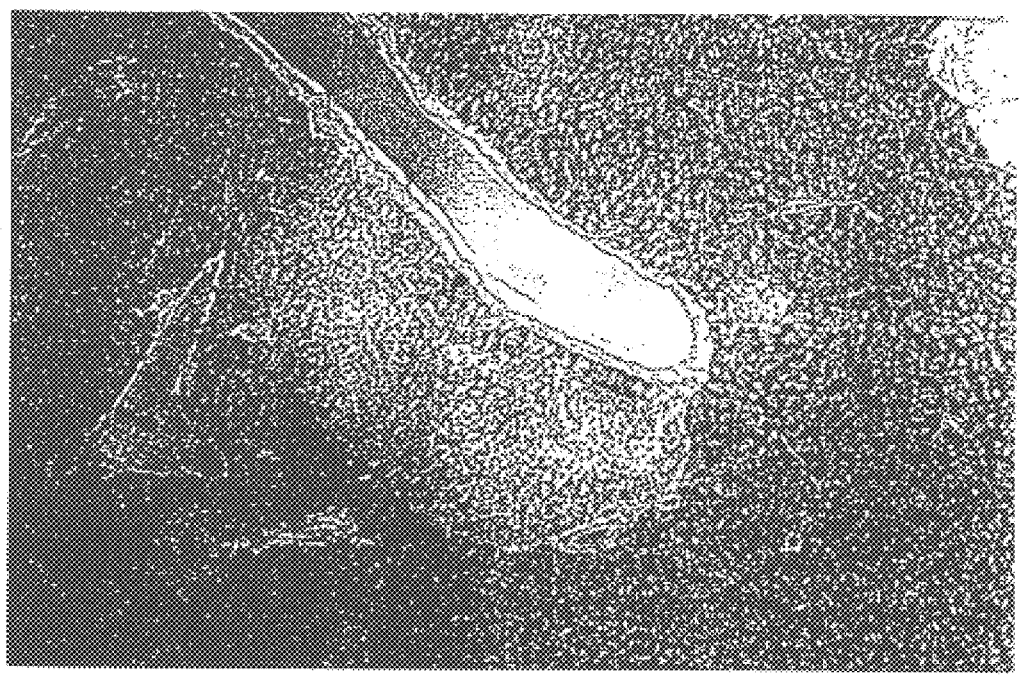
FIG. 2 is a half-tone reproduction depicting immunohistochemical staining for FAH of pancreas tissue from a wild-type adult mouse. This animal was age-, sex- and strain-matched to the animals used for isolating pancreatic cells. No positive FAH staining was observed, indicating that normal pancreatic cells do not express FAH.
Figure 3:
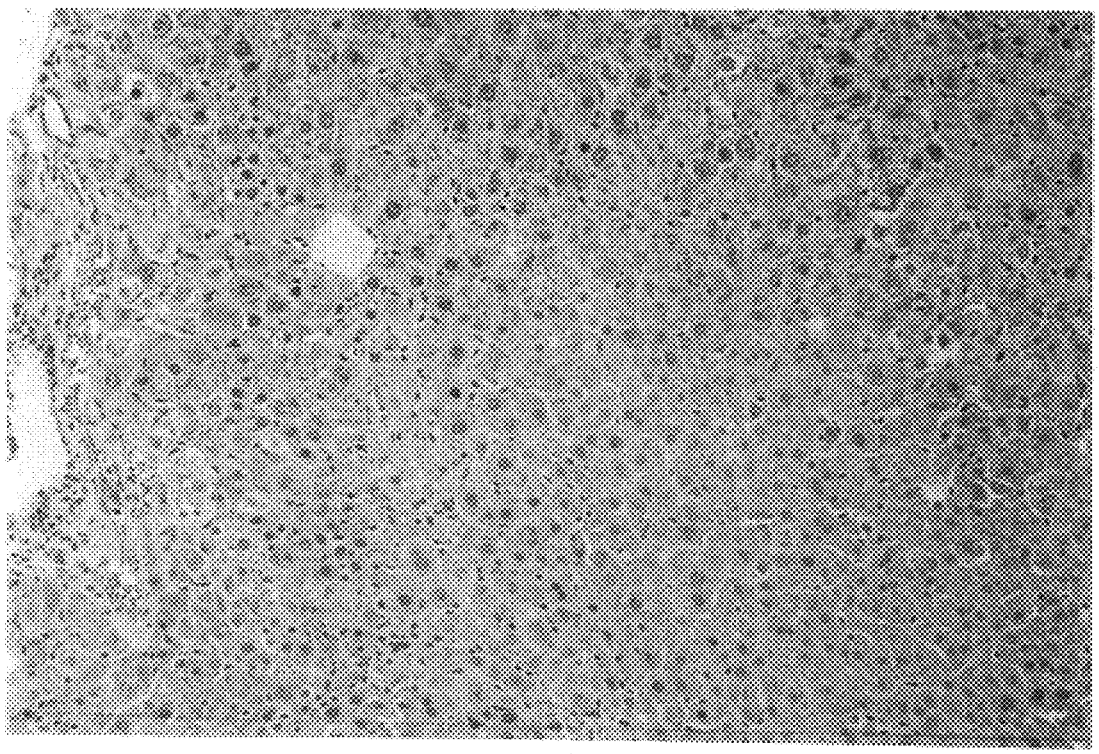
FIG. 3 is a half-tone reproduction depicting hematoxylin and eosin (H & E) staining of liver tissue from an FAH mutant mouse which has been repopulated with wild-type pancreas cells. At 200× magnification, the hepatocytes appear normal.
Figure 4:
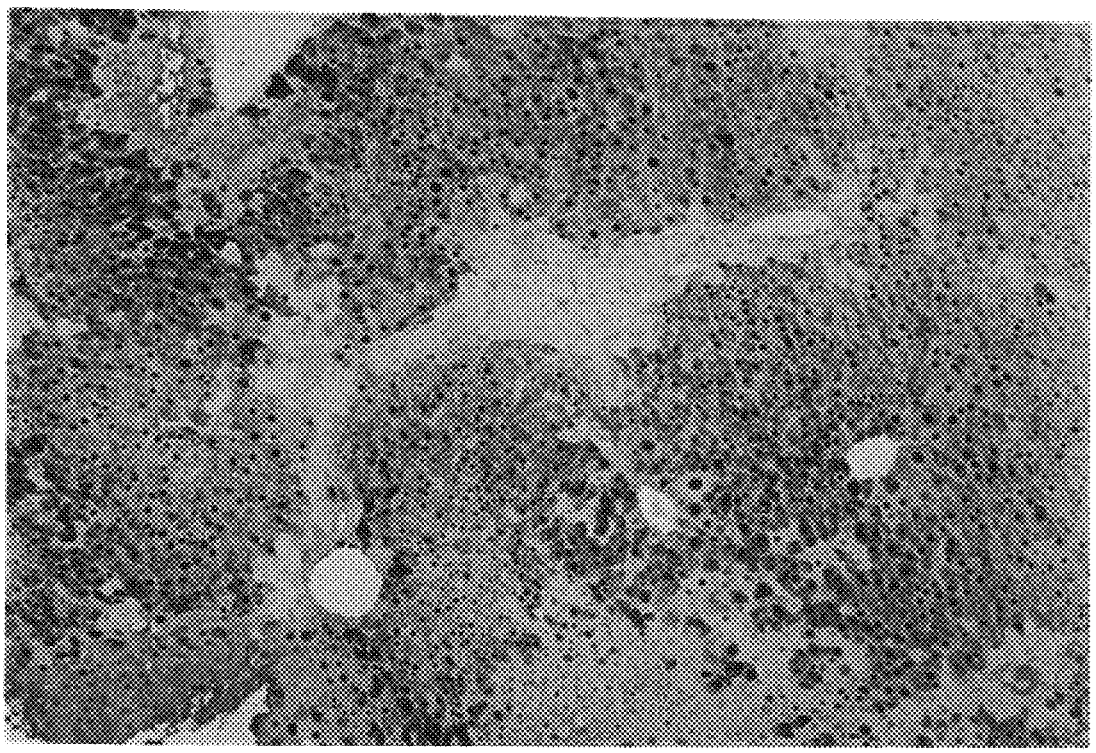
FIG. 4 is a half-tone reproduction depicting a 200× magnification immunohistochemical staining for FAH of liver tissue from an FAH mutant mouse which has been repopulated with wild-type pancreas cells. The majority of the hepatocytes stain positive for FAH.
Figure 5:
FIG. 5 is a half-tone reproduction depicting H & E staining of liver tissue from an FAH mutant mouse which has been repopulated with wild-type pancreas cells. At 100× magnification, the hepatoctyes appear normal.
Figure 6:
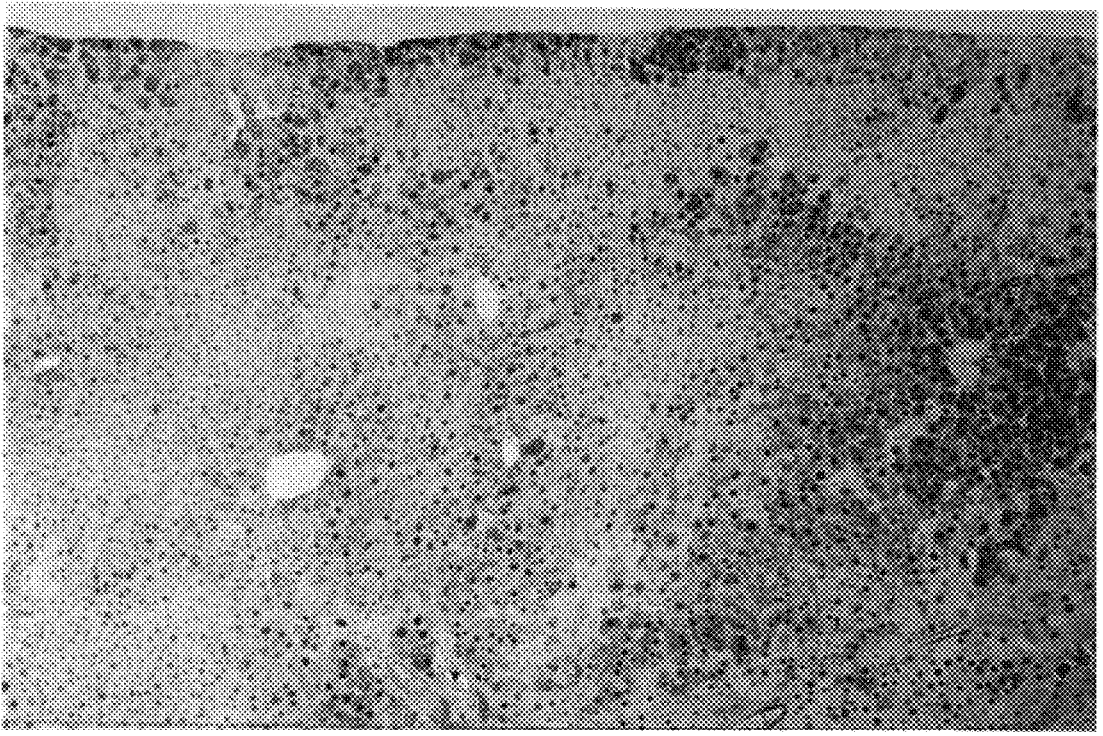
FIG. 6 is a half-tone reproduction depicting a 100× magnification immunohistochemical staining for FAH of liver tissue from an FAH mutant mouse which has been repopulated with wild-type pancreas cells. The majority of the hepatocytes stain positive for FAH.

In one embodiment, an effective amount of pancreas cells of the present invention are introduced into an individual and allowed to proliferate as described herein. FIG. 1 shows that the introduction of wild-type pancreas cells into the spleen of an FAH-mutant mouse produces FAH positive cells. Wild-type pancreas cells do not express FAH. (FIG. 2). Thus, the positive staining seen in FIG. 1 demonstrates that the pancreatic precursor cells have differentiated into hepatocytes after being introduced into the mutant mouse. As shown in FIGS. 3 and 5, introduction of wild-type pancreas cells into FAH mutant mice gives rise to liver cells which stain with hematoxylin and eosin (H & E). The liver tissue of FAH mutant mice does not normally stain with H &E. Similarly, FIGS. 4 and 6 show positive staining with FAH of liver tissue of a mutant FAH mouse into which wild-type pancreas cells have been introduced. Thus, using the present invention, cells expressing liver-specific markers are expressed.

Moreover, the methods of the present invention also give rise to functioning liver tissue. Without administration of the drug NTBC, FAH mutant mice exhibit severe liver dysfunction, resulting in death. Using the methods described herein, after introduction of pancreas cells, the FAH mutant mice survive when taken off NTBC. These mice also exhibit normal liver histology and normal liver function as assayed using by testing serum aspartate transaminase (AST) levels, bilirubin levels and by assaying plasma amino acid profiles.

Treatment of Liver Disease

Many liver diseases can be treated using the methods of the present invention. As described above, liver disorders include genetic conditions such as hereditary tyrosinemia type I (HT1) as well as acquired disorders such as hepatitis, cirrhosis, cancer and the like. The methods described herein are effective at regenerating liver function regardless of the disease or its mechanism of action.

In vitro Uses for Liver regenerating-Pancreas Cells

The pancreas cells of the present invention are also useful in developing in vitro systems in which to assay liver function or produce liver specific factors. The pancreas cells can be cultured in vitro under conditions which produce hepatocytes. Conditions for both long-term proliferation and differentiation can be determined by those of skill in the art. (See, e.g WO 94/16059 for long-term culture conditions for neuronal stem cells). Using appropriate in vitro culture systems, the pancreas cells would form a sort of "artificial liver" in culture which could produce, for example, liver specific enzymes. These systems could also be used to determine the effect of various treatments on the liver tissue and function.

The following examples are intended to illustrate the invention and are not intended to be limiting in any respect.

EXAMPLES

Example 1

Isolation of Pancreas Cells

A wild-type mouse, 129SU strain, ROSA-26 transgene marker, female, 22 grams was killed by cervical dislocation. The pancreas was identified by its yellow color, lumpy appearance and location on the inferior aspect of the spleen and was dissected out of the mouse. The pancreas was minced in EBSS (no calcium or magnesium) using scissors and scalpels. The minced pancreas was washed two times in EBSS.

The minced pancreas was then resuspended in 15 mL of collagenase (2 mg/mL collagenase type D, Boehringer-Mannheim in EBSS with 0.2 g/L $CaCl_2$ 0.1 g/L $MgSO_4$ and 10 mM HEPES). The suspension was transferred into a sterile 100 mL tissue culture media bottle and incubated with agitation at 37° C. for 30 minutes. Dissociation was aided by pipetting vigorously every 10 minutes.

Following the 30 minute incubation, the suspension was centrifuged at 2,000 rpm. The collagenase-containing supernatant was removed and the cells washed with EBSS. The tissue was resuspended in 10 mL of 0.25% trypsin/EDTA (Gibco) and transferred to a sterile 100 mL tissue culture media bottle. The suspension was incubated with agitation for 3 minutes at 37° C. The tissue was vigorously pipetted every 1 minute while in the trypsin solution.

The trypsin solution was neutralized with an equal volume of Dulbecco's minimal essential medium (DMEM) with 10% fetal calf serum, 50 U/mL penicillin, 50 μg/mL streptomycin base and 0.1 mg/mL DNAse I (Sigma, St. Louis, Mo.).

The suspension was filtered through a sterile nylon mesh after vigorous pipetting. The cells were centrifuged at 1,500 rpm and resuspended in DMEM with 10% fetal calf serum and penicillin/streptomycin. The cells were maintained on ice. Viability and clumpiness were estimated. Viability was estimated by trypan blue exclusion and was above 95%. A single pancreas yielded about $1 \times 10^6$ large cells and $2 \times 10^6$ smaller cells. The larger cells can be isolated by a 50 g centrifugation for 1 minute.

Example 2

Introduction of Pancreas Cells into Mice with Diseased Livers

Cell suspensions were isolated as described in Example 1 and were diluted to a density of $1 \times 10^6$ cells/mL in DMEM with 10% fetal calf serum. A 2–3 month old $FAH\Delta^{exon5}$ mutant mouse was anaesthetized with an intraperiotoneal injection of Avertin. The upper left abdominal quadrant of the animal was shaved and sterilized with an iodine solution. A small vertical incision was made in the skin and underlying muscle to expose the spleen of the anesthetized animal. Approximately 200 μl of the resuspended cells were taken up in a 1 mL syringe. A 30 gauge needle was used to slowly inject the 200 μl into the exposed spleen. The injection site was ligated using 5.0 silk sutures. The abdominal incisions were closed and the animal allowed to recover from anesthesia. The transplanted mouse was immediately taken off NTBC therapy immediately after the transplantation and in vivo selection is allowed to occur for 6–8 weeks after transplantation. The mutant mouse survived the selection period, indicating normal liver function. In addition, plasma ALT levels and plasma bilirubin levels were measured and found to be normal.

The structure of the regenerated liver is also determined. After the 6–8 week selection period, the surviving mice are examined for liver tissue by exposing the abdominal cavity. The tissue which appears as liver tissue (dark red, lobular) is removed and processed for further histological examination.

What is claimed is:

1. A method of regenerating liver function in an individual, the method comprising
   (a) introducing an effective amount of pancreas cells into the spleen of the individual, wherein said pancreas cells are derived from the same species as the individual; and
   (b) allowing the pancreas cells to regenerate at least one liver function selected from the group consisting of interconversion of metabolites, blood protein manufacture, erythropoietic function, detoxification, bile formation and vitamin storage.

2. The method according to claim 1 wherein the individual is a mammal.

3. The method according to claim 2 wherein the mammal is a human.

4. The method according to claim 1 wherein the pancreas cells are an autograft.

5. The method according to claim 1 wherein the pancreas cells are obtained from an in vitro culture.

6. The method of claim 1, wherein between about $10^3$ to about $10^{12}$ pancreas cells are introduced into the spleen of the individual.

7. The method of claim 6, wherein between about $10^6$ to about $10^9$ pancreas cells are introduced into the spleen of the individual.

8. The method of claim 1, wherein said introducing is accomplished by injecting said pancreas cells into the spleen of the individual.

9. A method of ameliorating symptoms of a liver disease in an individual, the method comprising:
   introducing pancreas cells into the spleen of the individual, wherein the pancreas cells are derived from the same species as the individual and are capable of regenerating at least one liver function selected from the group consisting of interconversion of metabolites, blood protein manufacture, erythropoietic function, detoxification, bile formation and vitamin storage; and
   ameliorating symptoms of said disease, wherein said amelioration is effected by the regeneration of said at least one liver function.

10. The method according to claim 9 wherein the individual is a human.

11. The method according to claim 9 wherein the pancreas cells are an autograft.

12. The method according to claim 9 wherein the pancreas cells are obtained from an in vitro culture.

13. The method of claim 9, wherein between about $10^3$ to about $10^{12}$ pancreas cells are introduced into the spleen of the individual.

14. The method of claim 9, wherein between about $10^6$ to about $10^9$ pancreas cells are introduced into the spleen of the individual.

15. The method of claim 9, wherein said introducing is accomplished by injecting said pancreas cells into the spleen of the individual.

16. The method of claim 9, wherein the liver disease is selected from the group consisting of hereditary tyrosinemia type I (HT1), hepatitis, cirrhosis, and cancer.

* * * * *